United States Patent [19]

Ushizawa et al.

[11] Patent Number: 4,957,615

[45] Date of Patent: * Sep. 18, 1990

[54] OXYGEN SENSOR

[75] Inventors: Norihiko Ushizawa, Fujinomiyashi; Takeshi Shimomura, Fujinomiya, both of Japan

[73] Assignee: Terumo Kabushiki Kaisha, Tokyo, Japan

[ * ] Notice: The portion of the term of this patent subsequent to Aug. 29, 2006 has been disclaimed.

[21] Appl. No.: 228,231

[22] Filed: Aug. 4, 1988

Related U.S. Application Data

[63] Continuation-in-part of Ser. No. 8,365, Jan. 29, 1987, abandoned.

[30] Foreign Application Priority Data

Feb. 4, 1986 [JP] Japan ................................ 61-22509

[51] Int. Cl.$^5$ ............................................. G01N 27/31
[52] U.S. Cl. .................................... 204/415; 204/414; 204/424; 204/431
[58] Field of Search ............... 204/424, 415, 1 P, 431, 204/414; 128/635

[56] References Cited

U.S. PATENT DOCUMENTS

| | | | |
|---|---|---|---|
| 4,198,851 | 4/1980 | Janata | 73/23 |
| 4,615,954 | 10/1986 | Solomon et al. | 429/27 |

*Primary Examiner*—G. L. Kaplan
*Attorney, Agent, or Firm*—Burns, Doane, Swecker & Mathis

[57] ABSTRACT

An oxygen sensor includes an electrically conductive substrate directly coated with an electrolytic oxidative polymeric membrane, which contains a porphyrin compound and a metal complex thereof. Also provided is an oxygen sensor capable of being subjected to a temperature calibration and including an oxygen electrode consisting of an electrically conductive substrate directly coated with a porphyrin derivative compound and a metal complex compound thereof, a reference electrode, a gelled polymeric electrolyte in which the oxygen electrode and reference electrode are immersed, and an oxygen-selective permeable membrane coating the gelled polymeric electrolyte. The electrically conductive substrate according to the present invention is formed from a material inactive with oxygen gas, such as indium tin oxide, iridium oxide, nickel or gold.

8 Claims, 18 Drawing Sheets

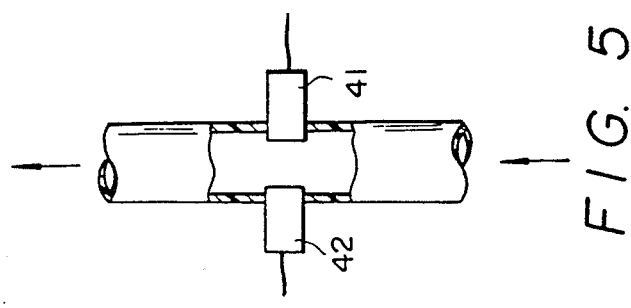
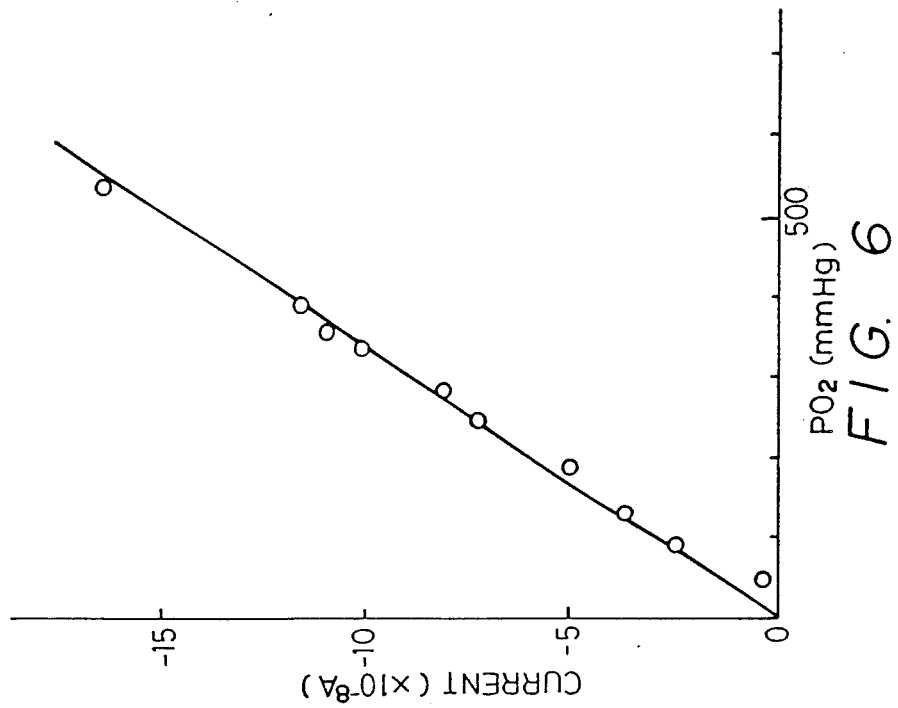

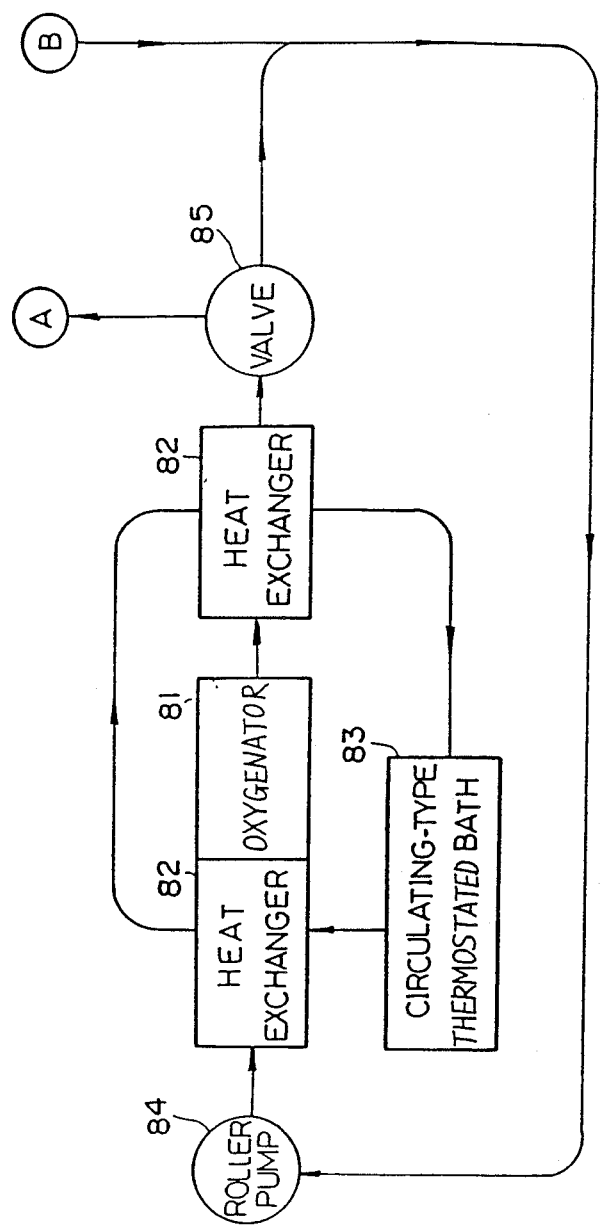

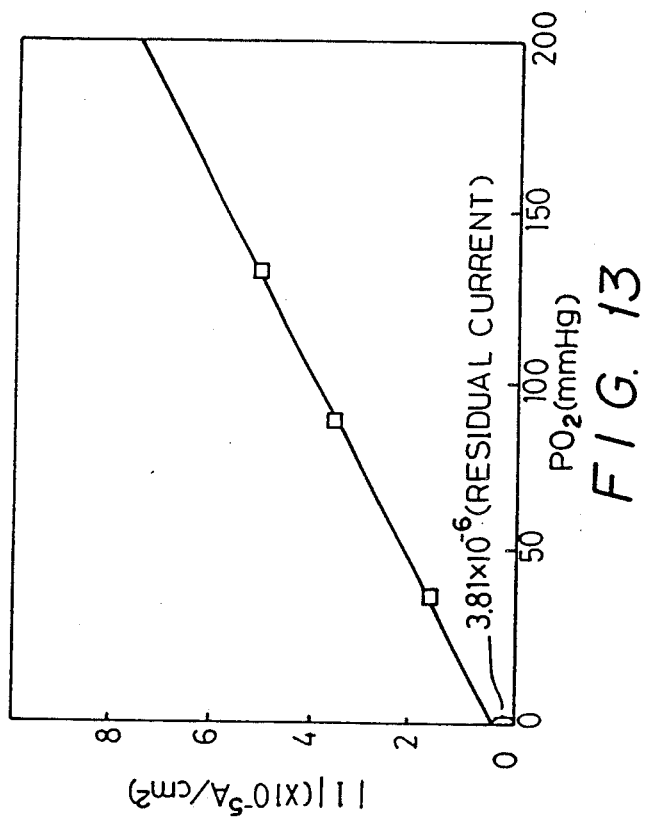

OXYGEN SENSOR

CROSS REFERENCED RELATED APPLICATIONS

The present application is a continuation-in-part of Ser. No. 008,365, filed Jan. 29, 1987 and now abandoned.

BACKGROUND OF THE INVENTION

1. Field of the Invention:

This invention relates to an oxygen sensor, and more particularly, to a solid-state and Clark type oxygen sensor used to measure, by way of current response, the concentration of oxygen dissolved in a solution.

2. Description of the Prior Art:

Oxygen electrodes used as oxygen sensors may be classified roughly into two types. These are:

(i) an internal liquid-retaining type having an internal electrolyte chamber separated from the liquid specimen such as by a polymeric membrane, and (ii) a separating type in which a noble metal such as platinum is coated with a glass or polymeric membrane that is selectively gas-permeable.

However, the internal liquid retaining-type oxygen electrode (i) is disadvantageous in that (1) the membrane is readily damaged, (2) the internal electrolyte chamber is readily contaminated, and (3) miniaturization of the electrode is difficult. For these reasons, the separating-type electrode (ii), particularly solid-state electrodes, are drawing attention for use as oxygen sensors in the medical field.

One example of a solid-state electrode which can be mentioned is one obtained by depositing an oxygen-selective separating membrane on the surface of platinum. However, the electrode has the following drawbacks:

(1) The separating membrane is required to have a membrane thickness of 0.5–50 $\mu$m in order to enhance its separating performance. Consequently, time is required for the oxygen to reach the surface of the platinum, thus resulting in a slow speed of response (usually 5 min).

(2) When immersed in a liquid specimen for an extended period of time in order to perform a continuous measurement, the electrode is influenced by interfering ions in the specimen. This means that a calibration curve prepared in advance can no longer be used.

(3) As a consequence of (2) above, long-term measurement requires that the electrode be extracted from the system and recalibrated. Thus, difficulties are encountered in terms of use.

In an effort to solve the foregoing problems, Japanese Pat. Application Laid-Open (KOKAI) No. 60-52759 proposes an oxygen sensor using electrically conductive carbon in place of platinum and a metal complex, which serves as a catalyst for the reduction reaction of oxygen, as an oxygen-selective separating membrane, with the metal complex being deposited on the surface of the electrically conductive carbon.

However, since the membrane of this oxygen sensor is formed by e.g. coating the conductive carbon with a solution of the metal complex followed by drying, the metal complex tends to elute into the liquid specimen. Though such elution is prevented by providing the sensor with an elution preventing layer such as Nafion R, the latter interacts with charged substances other than oxygen, as a result of which the oxygen sensor loses its selectivity.

An oxygen sensor available on the market is of the Clark type, in which silver/silver chloride is used as a reference electrode, platinum or platinum black is used as a working electrode, the electrodes are submerged in an alkaline solution such as a KOH solution, and the outside is coated with a silicone film. However, shortcomings encountered with this sensor include leakage and contamination of the internal liquid chamber of the electrode.

For continuous monitoring in a circulating system, the need for smaller, more durable electrodes having such characteristics as temperature compensation is emphasized. Recently, coated wire-type oxygen sensors in which a platinum electrode is directly coated with a cellulose membrane or other polymeric membranes have appeared on the market in the form of electrodes for testing purposes. These sensors exhibit durability problems and the period over which they can be used is shortened in areas of high $PO_2$. (In an oxygenator, for example, this can be as high as 350 mmHg–760 mmHg, depending upon the particular case.) This can be thought of as being a problem in terms of durability. An oxygen sensor usable in a circulating system has not yet been marketed or developed.

SUMMARY OF THE INVENTION

Accordingly, the inventor has performed exhaustive research in an effort to eliminate the aforementioned defects of the conventional oxygen sensors. As a result of this research, the inventor has discovered that an oxygen sensor with excellent selectivity and having a membrane component that will not elute can be obtained if an oxidative polymeric membrane of a porphyrin compound having, as a substituent, a phenyl radical possessing an active group such as OH or $NH_2$, or of a complex in which the porphyrin compound serves as a liquid, is used as the coating membrane. The invention has been perfected on the basis of this discovery.

More specifically, according to the present invention, there is provided an oxygen sensor comprising an electrically conductive substrate and an electrolytic oxidative polymeric membrane coating the surface of the electrically conductive substrate. The electrolytic oxidative polymeric membrane comprises at least one substance selected from a porphyrin compound and a metal complex thereof.

Preferably, the electrically conductive substrate used in the oxygen sensor of the invention is inactive with oxygen gas. Preferred examples of inactive materials for the electrically conductive substrate are electrically conductive carbon, indium tin oxide, iridium oxide, nickel and gold. Examples of electrically conductive carbon are basal plane, pyrolytic graphite ("BPG"), glassy carbon and the like.

Preferred examples of the porphyrin compound used in the oxygen sensor of the present invention are porphyrin compounds in which a hydroxy aromatic derivative is substituted at the meso-position and porphyrin compounds in which an amino aromatic derivative is substituted at the meso-position.

Preferred examples of the metal complex of the porphyrin compound used in the oxygen sensor of the present invention are a porphyrin metal complex in which a hydroxy aromatic derivative is substituted at the meso-position and metallo-porphyrin complexes in which an amino aromatic derivative is substituted at the meso-position.

Examples of the porphyrin compound having a hydroxy aromatic derivative or amino aromatic derivative substituted at the meso-position are tetra-, tri-or mono-(hydroxyphenyl) porphyrin, tetra-, tri- or mono-(aminophenyl) porphyrin, etc., expressed by the formula

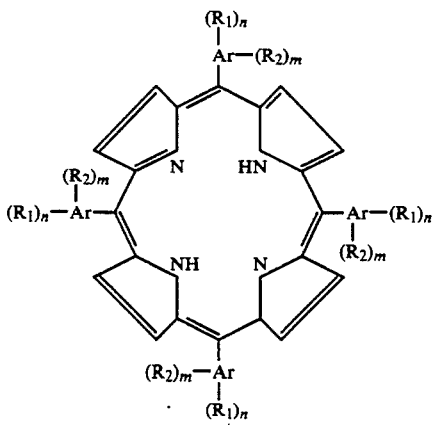

where Ar represents an aromatic series, $R_1$ a substituent group which participates at the time of electrolytic oxidative polymerization, $R_2$ a substituent group which does not participate in electrolytic oxidative polymerization, and, in principle, n is 1 or the effective valance of Ar and m is 0 or the effective valence $-1$ of Ar. The hydroxyl group- and amino group-substituted positions preferably are the ortho-and para-positions. It is also permissible to substitute the hydroxyl and amino group or other substituent groups at other positions.

Examples of the metal complex of the porphyrin compound having a hydroxy aromatic derivative or amino aromatic derivative substituted at the meso-position are tetra-, tri- or mono(hydroxyphenyl) porphyrin complexes, tetra-, tri- or mono(aminophenyl) porphyrin complexes, etc., expressed by the formula

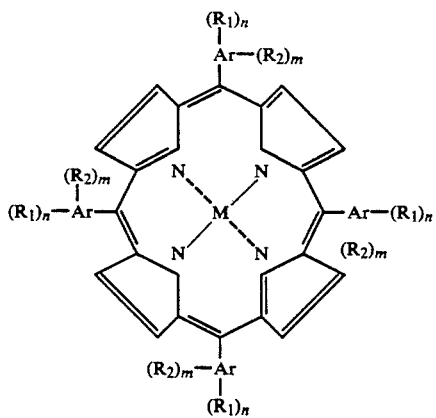

where Ar represents an aromatic series, $R_1$ a substituent group which participates in electrolytic oxidative polymerization, $R_2$ a substituent group which does not participate in electrolytic oxidative polymerization, and, in principle, n is 1 or the effective valance of Ar and m is 0 or the effective valence $-1$ of Ar. Examples of the complex-forming metal are transition metals such as titanium, vanadium, chromium, manganese, iron, cobalt, nickel, copper, ruthenium, rhodium, palladium, osmium, iridium, platinum, silver and gold, as well as zinc or tin. Especially preferred are cobalt, nickel, iron, copper, manganese, chromium and platinum.

To deposit the electrolytic polymeric membrane consisting of the porphyrin, or the metal complex thereof, having the hydroxy aromatic derivative or amino aromatic derivative substituted at the meso-position on the surface of the electrically conductive carbon substrate, electrolytic oxidative polymerization is carried out with the carbon substrate immersed in an electrolyte solution including at least one of the above-mentioned porphyrin compounds or metal complexes thereof and containing a supporting electrolyte. Examples of the solvent used in electrolyte solution are acetonitrile, methanol, dimethyl formamide, dimethyl sulfoxide, propylene carbonate and the like. Preferred examples of the supporting electrolyte are perchlorates, sulfuric acid, phosphoric acid, boric acid, tetrafluoro-potassium phosphate, quaternary ammonium salts and the like. It is preferred that the electrolytic oxidative polymeric membrane have a membrane thickness of 0.01–50 $\mu$m.

Since the deposited electrolytic oxidative polymeric membrane has denseness and does not readily elute into a liquid specimen, ordinarily it can be used without depositing another membrane thereon. However, when taking a measurement in a body fluid such as blood or urine, it is preferred that a regenerated cellulose membrane, acetyl cellulose, polystyrole, polyhydroxyethyl methacrylate or the like be deposited before on the above membrane before use in order to prevent the adhesion of proteins and the penetration of reduced substances. The preferred membrane thickness of this deposited material is 0.5–50 $\mu$m.

Since the electrolytic oxidative polymeric membrane of the invention is oxidized upon contacting oxygen, a current based on the reduction reaction of the electrolytic oxidative polymeric membrane is observed when a fixed potential is applied using the oxygen sensor of the invention as a working electrode. Accordingly, if a correlation can be obtained beforehand between the oxygen concentration in a standard solution and the observed current value, then the oxygen concentration can be determined from the observed current value when measurement is taken in the liquid specimen.

Though the potential applied to the working electrode differs depending upon the type of porphyrin compound or complex thereof used in the coating membrane and upon the membrane formation method, it is especially preferred that the potential be taken to have a negative value with respect to the peak potential of the oxygen reduction current in a cyclic voltammogram, of the type shown in FIG. 3, as will be described below.

The oxygen sensor of the invention having the above-described construction has the following advantages:

(1) Since the solid-state, membrane-coated electrode does not employ an internal liquid, there is no internal contamination as occurs in a conventional Clark-type electrode having an internal liquid chamber. This eliminates the troublesome task of replacement. Absence of the internal chamber also makes it possible to miniaturize the sensor.

(2) Since the electrode substrate is electrically conductive carbon, costs are reduced over the prior-art arrangement that relies upon a noble metal. The oxygen sensor is therefore suitable for disposable use.

(3) Since the sensor comprises the electrode substrate (electrically conductive carbon, indium tin oxide, iridium oxide, gold, nickel and the like) directly coated with the polymeric membrane of an oxygen reducing species (porphyrin) using an electrolytic polymerization process, a number of advantages are gained in comparison with the conventional electrode coated with a membrane having an oxygen reducing species carried in a polymeric membrane. These advantages are as follows:

(1) The concentration of the oxygen reduction reaction species in the membrane can be raised, and a dense membrane can be formed. Accordingly, a thin membrane will suffice so that the response time with respect to oxygen can be shortened.

(2) The sensor has excellent selectivity to oxygen since no interfering substances are taken in.

(3) Since the membrane itself is solvent resistant, the metal complex does not elute into the liquid specimen. This generally dispenses with the need to deposit an additional membrane such as an elution preventing membrane and simplifies the overall structure.

(4) The sensor can be stored in the dry state and can be submitted to use directly from storage. This enables oxygen concentration to be measured without delay.

According to the present invention, the above object is attained by providing an oxygen sensor comprising an oxygen electrode consisting of an electrically conductive substrate directly coated with a porphyrin derivative compound and a metal complex compound thereof, a reference electrode, a gelled polymeric electrolyte in which the oxygen electrode and reference electrode are immersed, and an oxygen-selective permeable membrane coating the gelled polymeric electrolyte.

An example of an oxygen-selective permeable membrane for use in the present invention is made of a hydrophobic polymeric membrane such as Silicone, polypropylene, polyethylene and Teflon.

Examples of an electrically conductive substrate ideal for use in this aspect of the present invention are electrically conductive carbon, indium tin oxide, iridium oxide, gold, nickel and the like.

An example of a porphyrin derivative ideal for use in the invention is a meso-type phenyl derivative. Ideal porphyrin complexes are Fe, Co and Ni.

The features of the oxygen sensor according to this aspect of the invention are as follows:

(1) The amount of oxygen dissolved in solution ($PO_2$ mmHg) is measured from the reducing current at the membrane surface of the poly(porphyrin) and metal complex thereof.

(2) In such case, a linear relationship holds between the current value (current density) and $PO_2$ even when the measurement temperature (15°–45° C.) is varied. Within this temperature region, therefore, temperature compensation is possible by way of four-point calibration based on $PO_2$ (two points) and the temperature change (two points).

(3) Under conditions of constant temperature $PO_2$ (mmHg) can be calibrated from (2) above. Accordingly, the oxygen sensor of the invention is one that makes measurement of $PO_2$ in a continuous system possible.

The oxygen sensor according to this aspect of the invention has the following advantages:

(1) Temperature compensation is possible.

(2) The $PO_2$ (mmHg) - reducing current correlation exhibits good linearity at a constant temperature. This enables the $PO_2$ concentration to be measured from this calibration curve.

(3) The oxygen sensor can be used in a circulating system.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 5 is an enlarged view of a portion of the flow-through cell of FIG. 4;

FIG. 6 is a plot of current values against $PO_2$ obtained using the oxygen sensor fabricated in accordance with the first embodiment;

FIG. 13 is a plot of Current density against $PO_2$ at 25° C.;

DESCRIPTION OF THE PREFERRED EMBODIMENT

Example 1

Figure 1:
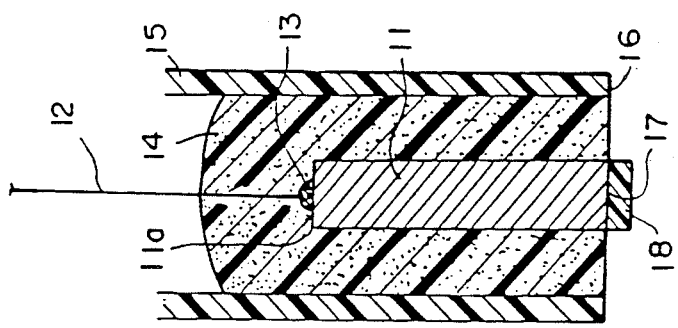
FIG. 1 is an enlarged sectional view illustrating an example of an oxygen sensor according to the present invention.

The electrode shown in FIG. 1 was fabricated through a process which will now be described with reference to the same Figure.

(i) Fabrication of carbon electrode

A copper wire 12 was fixed by means of an electrically conductive adhesive 13 (C-850-6, manufactured by Amicon) to the end face 11a of BPG 11 (transverse cross section: 0.25 mm×0.25 mm). This was followed by coating and insulating the periphery of the BPG 11 with an epoxy bonding agent 14 (TB 2067, manufactured by Three Bond Corp.) and a Teflon tube 15 (outer diameter: about 1.40 mm). The projecting tip 16 of the electrode thus fabricated was then cut away with a knife blade to expose a new BPG surface 17 for the purpose of forming an oxygen-sensitive portion. An electrolytic oxidative polymeric membrane 18 was formed on this exposed surface through the following process:

(ii) Electrolytic oxidative polymerization

Electrolytic oxidation was carried out under the following conditions using a three-electrode cell in which the carbon electrode fabricated in (i) above, a platinum coil and a silver/silver chloride electrode served as the working electrode, counter electrode and reference electrode, respectively:

| (Composition of electrolyte solution) | 10 mmol/l |
|---|---|
| tetra(o-aminophenyl) porphyrin | |
| sodium perchlorate | 0.1 mol/l |
| solvent: acetonitrile | |
| (Electrolytic conditions) | |

Figure 2:
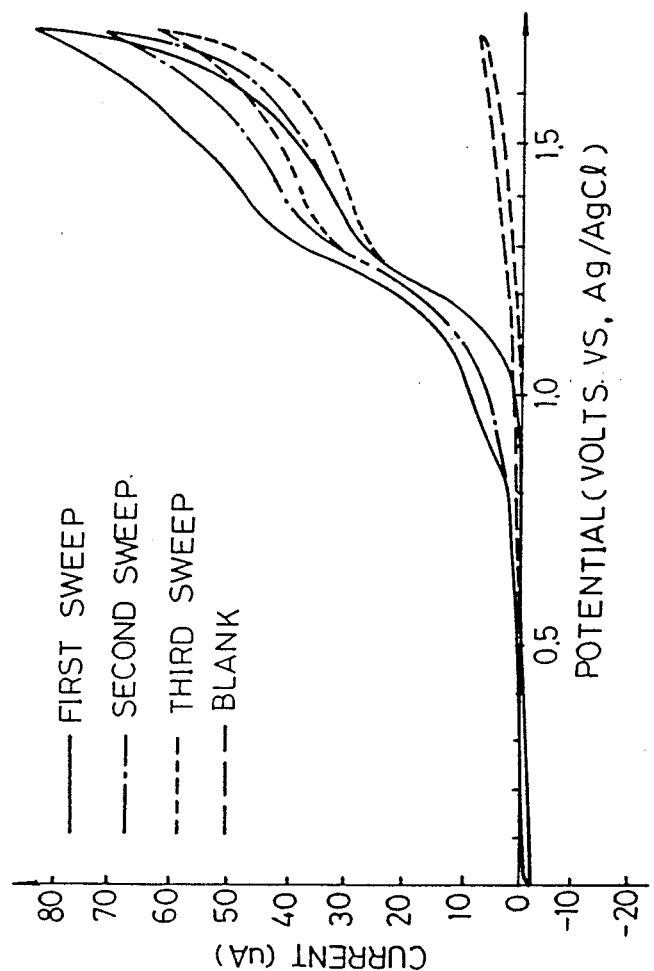
FIG. 2 is a cyclic voltammogram obtained when electrolytic polymerization is performed in accordance with a first embodiment of the invention.

The electrolyzing voltage was swept three times from 0 to 1.7 V (vs. Ag/AgCl), followed by carrying out constant-potential electrolysis for 1 hr at a constant potential of +1.7 V. A cyclic voltammogram obtained at this time is shown in FIG. 2. The membrane produced was light brown in color.

(Experiment 1)

A three-electrode cell was constructed using the oxygen sensor fabricated in accordance with Example 1, a platinum coil and a saturated sodium chloride calomel electrode (SSCE) as the working electrode, counter electrode and reference electrode, respectively. A cyclic voltammogram was obtained using 50 mmol/l of a phosphate buffer solution (pH 7.4, with addition of 0.154 mol/l NaCl). The sweep rate was 50 mV/sec.

Figure 3:
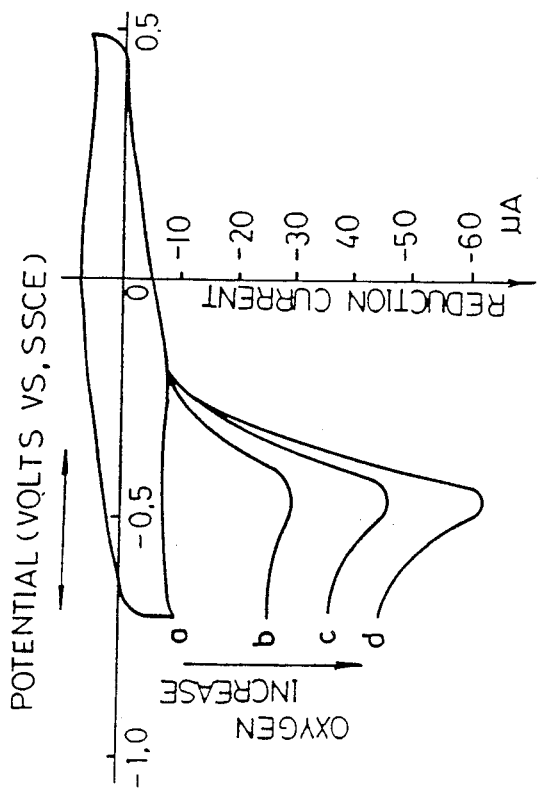
FIG. 3 is a cyclic voltammogram obtained by immersing an oxygen sensor fabricated in accordance with the first embodiment in solutions having different oxygen concentrations.

In accordance with the cyclic voltammogram (a) of FIG. 3 obtained under a condition where oxygen was removed by sufficient bubbling of the electrolyte solution with nitrogen, a peak does not appear in the 0.5–0.7 V range. When oxygen is added to the electrolyte solution, however, a peak appears in the vicinity of −0.45 V, and the peak current rises with an increase in the amount of dissolved oxygen in solution (b, c, d). It may thus be understood that the dissolved oxygen is being reduced at this potential.

(Experiment 2)

Figure 4:
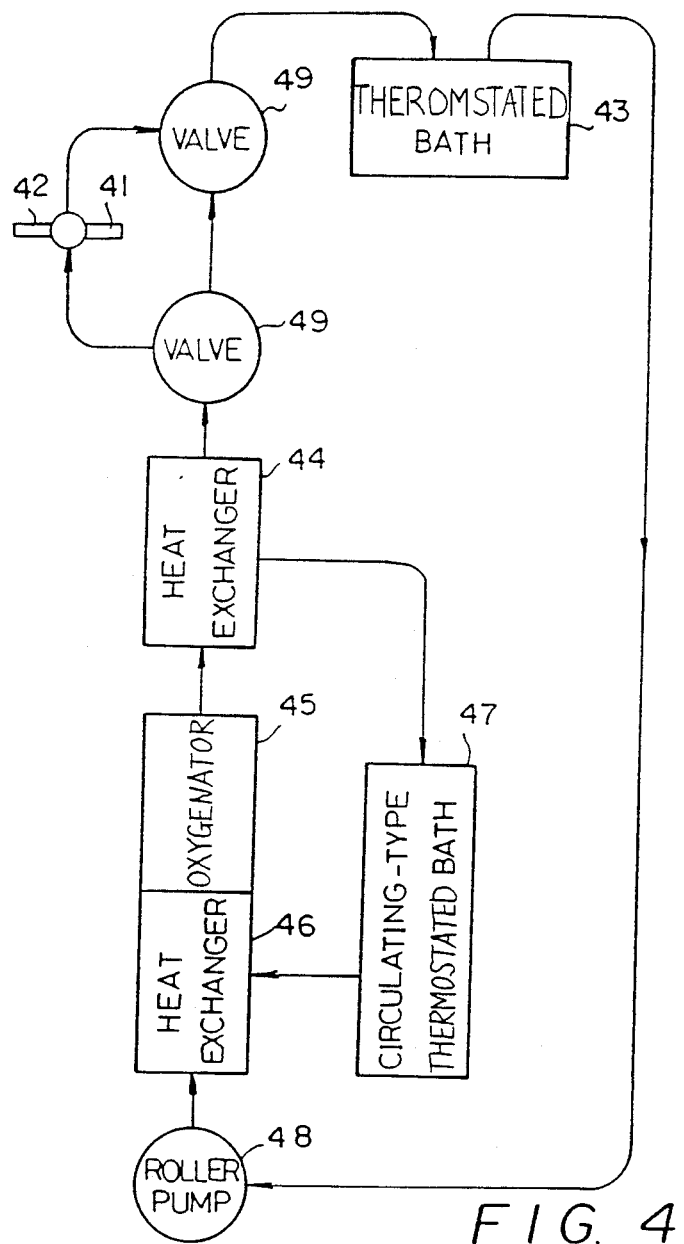
FIG. 4 is a circuit diagram of a flow-through cell.

50 mmol/l of a phosphate buffer solution (pH 7.44, with addition of 0.154 mol/l NaCl) was circulated in the flow-through cell of FIG. 4 at a flow rate of about 1 l/min. The oxygen sensor fabricated in accordance with Example 1 and an Ag/AgCl electrode were immersed in the circulating solution (FIG. 5). As shown in FIGS. 4 and 5, the flow-through cell includes an oxygen sensor 41, silver/silver chloride electrode 42, a thermostated bath 43, heat exchangers 44, 46, an oxygenator 45, a circulatory-type thermostated bath 47, and a roller pump 48.

The two electrodes were connected to an oxygen concentration measurement apparatus (model POG-201, manufactured by Unique Medical), and current values which prevailed when the sensor potential was regulated to −0.6 V (vs. Ag/AgCl) were measured while the partial pressure of oxygen (PO$_2$) in the circulating solution was varied from 50 to 600 mmHg. The partial pressure of oxygen was adjusted by varying the N$_2$/O$_2$ gas partial pressure ratio by a gas exchanger. A plot of current values against PO$_2$ at 37° C. is shown in FIG. 6.

As illustrated in FIG. 6, the plot exhibits good linearity over a wide range of PO$_2$ values of from 50 to 600 mmHg. The slope of the line is $3\times10^{-10}$ A/mmHg which, calculated in terms of current density, is $4.8\times10^{-7}$ A/cm$^2$ mmHg. It was found based on these facts that an excellent oxygen sensor exhibiting good sensitivity could be obtained.

(Comparative Example 1)

A plot (FIG. 7) of current values against PO$_2$ was obtained as in Experiment 2 using a membrane-coated platinum electrode (diameter: 0.08 mm, manufactured by Unique Medical).

Figure 7:
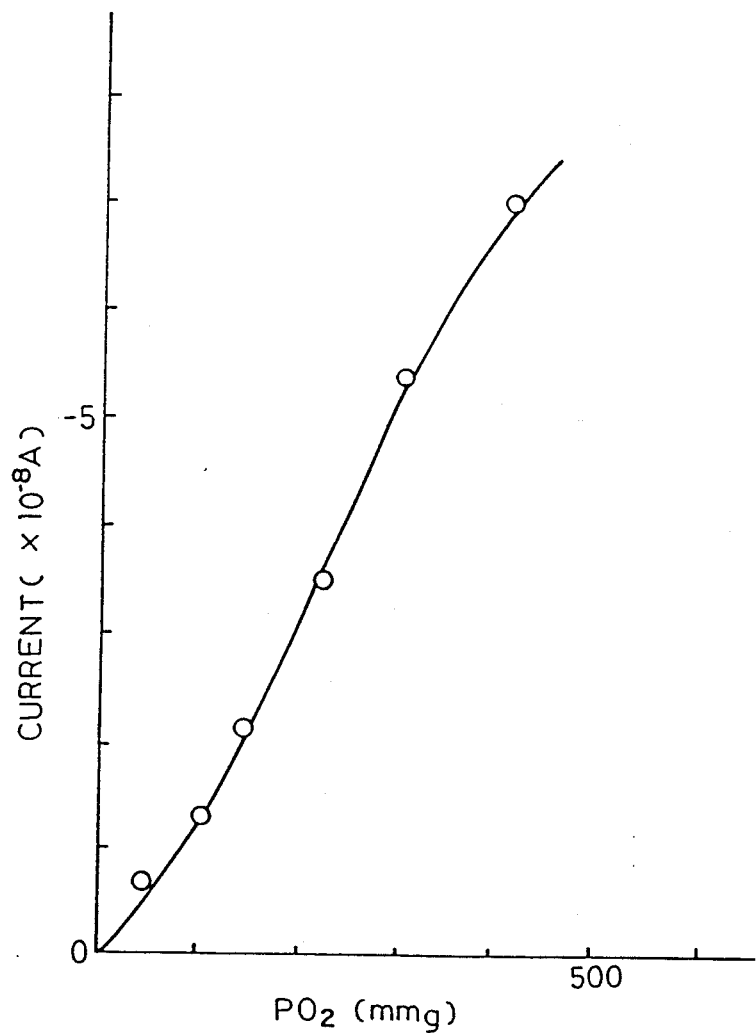
FIG. 7 is a plot of current values against $PO_2$ obtained using a membrane-coated platinum electrode.

As shown in FIG. 7, the plot exhibits curvature over a range of PO$_2$ values of from 50 to 400 mmHg.

(Experiment 3)

An oxygen sensor was fabricated by coating the electrode surface of the oxygen sensor fabricated in accordance with Example 1 with a decomposed regenerated cellulose membrane, drying the electrode and then depositing a regenerated cellulose membrane (membrane thickness: about 100 μm). The oxygen sensor was used to test the response thereof. The method used will now be described.

Experimental Method

Figure 8:
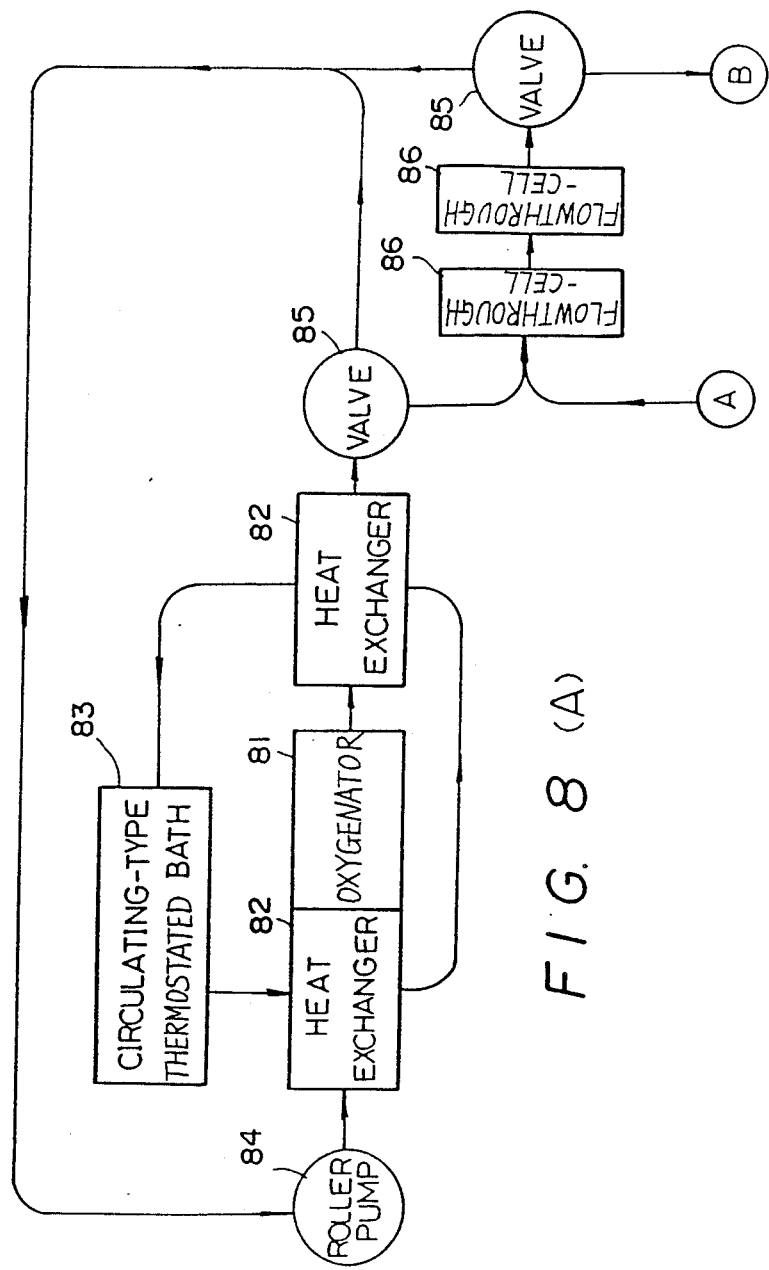
FIGS. 8(A) and 8(B) are diagrams of a circulating system for measuring response time with respect to $O_2$.
Figure 9:
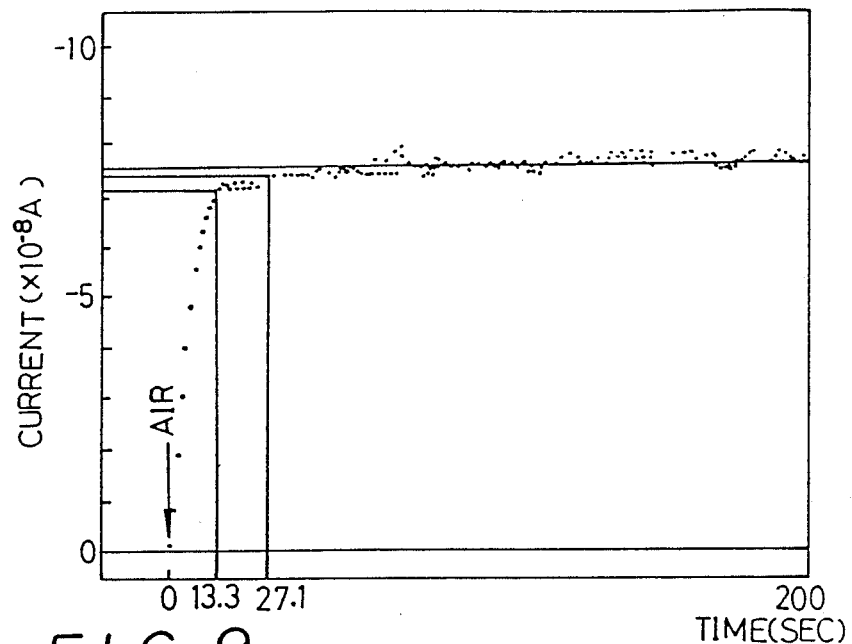
FIGS. 9 and 10 show current-time curves for the oxygen sensor of the present invention.
Figure 10:
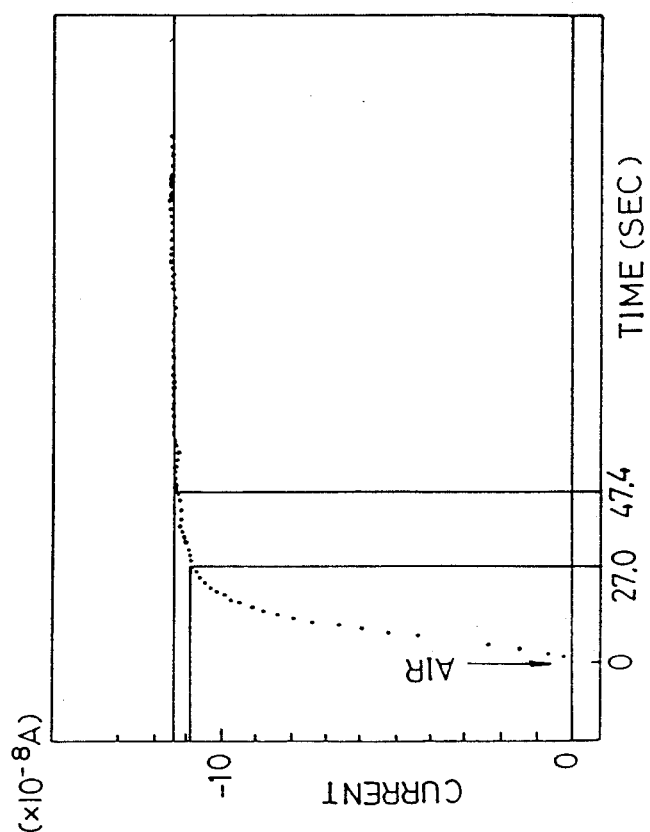

The above-mentioned oxygen sensor and an Ag/AgCl electrode were connected to an oxygen concentration measurement apparatus (model POG-201, manufactured by Unique Medical), and a measurement was taken in a circulating system of the kind shown in FIGS. 8(A) and 8(B). The system includes oxygenator 81, heat exchangers 82, circulatory-type thermostated baths 83, roller pumps 84, valve 85 and flow-through cells 86. Initially, 50 mmol/l of a phosphate buffer solution at PO$_2$=0 mmHg was circulated through the flow-through cells 86. Thereafter, the valves 85 were actuated and 50 mmol/l of the phosphate buffer solution at PO$_2$=143 mmHg was circulated through the flow-through cells 86. FIG. 9 shows the current-time curve obtained, and Table 1 shows the response times. It should be noted that FIG. 9 shows a curve observed under a condition where the time constant of the oxygen concentration measurement apparatus was 1 sec. The noise at the flat portion of the curve can be eliminated if the time constant is set to 5 sec (FIG. 10).

Example 2

Figure 19:
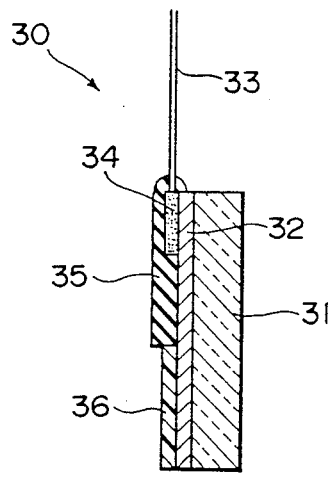
FIG. 19 is an enlarged sectional view illustrating the oxygen sensor according to Example 2 of the present invention.
Figure 20:
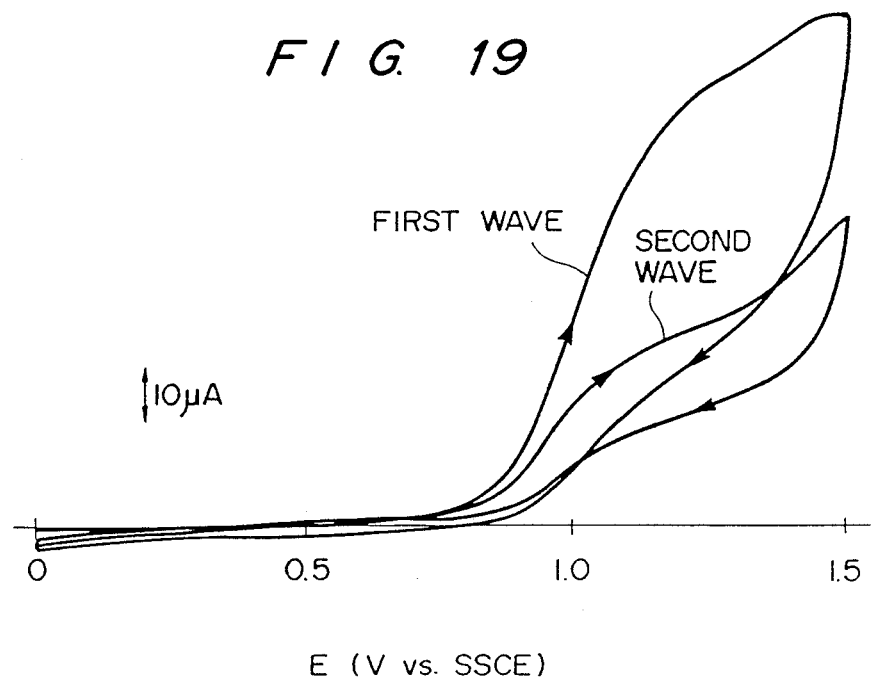
FIG. 20 is a cyclic voltammogram obtained when electrolytic polymerization is performed in accordance with this second embodiment of the invention.

FIG. 19 is a schematic sectional view illustrating an oxygen sensor in accordance with the present embodiment.

An ITO (indium tin oxide) electrode 32 was fabricated by depositing ITO on one surface of glass 31 by a vapor deposition process or the like, connecting a lead wire 33 to one end of the resulting product by an electrically conductive adhesive 34, and insulating the result with silicone 35 (SE9155, manufactured by Toshiba Silicone K.K.). Next, a polymeric membrane [meso-tetra(o-aminophenyl) cobalt porphyrin] 36 was deposited on the surface of the ITO electrode 32 under the following electrolytic conditions in a three-electrode cell using the ITO electrode, a saturated sodium chloride calomel electrode (SSCE) and a platinum mesh as an active electrode, reference electrode and opposing electrode, respectively:

| Electrolyte solution | |
|---|---|
| meso-tetra (o-aminophenyl) cobalt porphyrin | 1 mM/l |
| sodium perchlorate | 0.1 M/l |
| solvent: acetonitrile | |
| Electrolytic conditions | |

The electrolyzing voltage was swept three times from 0.0 to 1.5 V (vs. SSCE), followed by carrying out constant-potential electrolysis for 2 min at a constant potential of +1.5 V.

It was confirmed that, as a result of electrolysis, a light-brown polymeric membrane [meso-tetra(o-aminophenyl) cobalt porphyrin] (hereinafter referred to as "poly Co-TAPP") 36 was deposited on the surface of the ITO electrode 32.

(Experiment 10)

Figure 21:
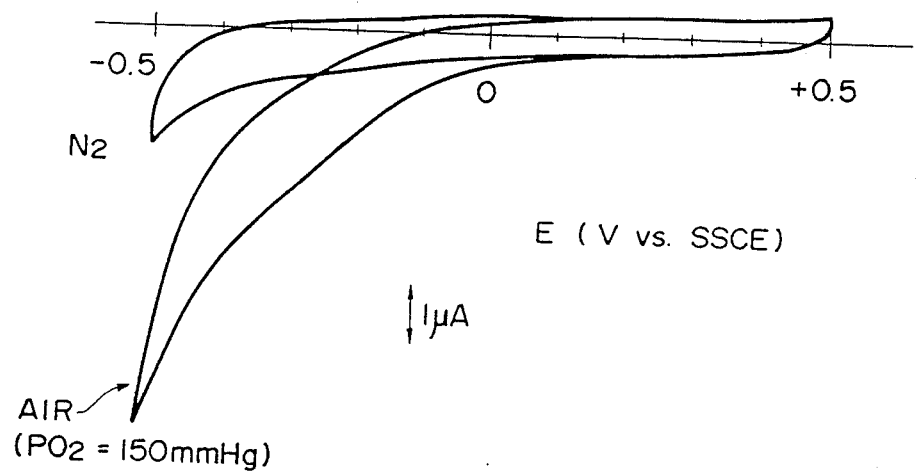
FIG. 21 is a cyclic voltammogram obtained by immersing an oxygen sensor fabricated in accordance with the second embodiment in solutions having different oxygen concentrations.

Next, reduction of residual oxygen in the aqueous solution of 0.2 M NaCl was investigated by a cyclic voltammogram using the (ITO/poly Co-TAPP) electrode 30 as the active electrode, SSCE as the reference electrode, and a platinum mesh as the opposing electrode. FIG. 21 clearly shows that in the case of $N_2$ substitution, the only current corresponds to residual current, while an oxygen reduction wave appears in case of air substitution ($PO_2=100$ mmHg, 25° C.). Accordingly, it was found that the (ITO/poly Co-TAPP) electrode 30 could be utilized as an oxygen sensor.

The ITO electrode 32 is one type of semiconductor. Results similar to those described above were obtained even when iridium oxide was used.

Example 3

Figure 11:
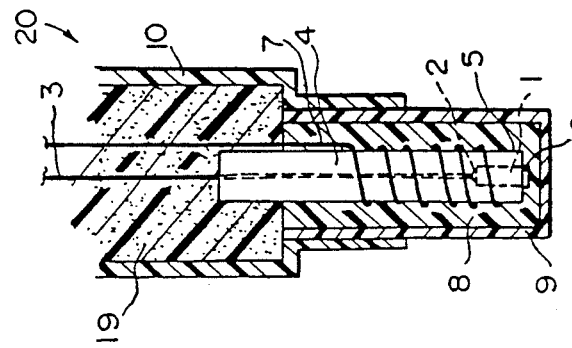
FIG. 11 is a schematic view illustrating the construction of an oxygen sensor fabricated in accordance with a third embodiment of the invention.

FIG. 11 schematically illustrates an oxygen sensor used in this embodiment. BPG 1 having a square cross section 0.5 mm on a side and a length of 3.0 mm served as the electrically conductive substrate, and a lead wire 3 was bonded to the substrate with an electrically conductive bonding agent 2 (C-850-6, manufactured by Amicon K.K.). The periphery was coated and insulated with an epoxy bonding agent 4 and a Teflon tube 5 having an inner diameter of 1 mm. Only the cross section of the BPG 1 functioned as the electrode surface. This electrode surface was coated with L an electrolytic polymeric membrane 6 of meso-tetra(o-aminophenyl) cobalt porphyrin under the following electrolytic conditions:

| (Composition of electrolyte solution) | 1 mmol/l |
|---|---|
| meso-tetra (o-aminophenyl) cobalt porphyrin | |
| sodium perchlorate | 0.1 mol/l |
| solvent: acetonitrile | |

| -continued | |
|---|---|
| (Electrolytic conditions) | |

The BPG electrode, an Ag/AgCl electrode and a platinum coil were used as the working electrode, reference electrode and counter electrode, respectively. With these electrodes immersed in the electrolyte, the electrolyzing voltage was swept three times from 0.0 to 1.8 V (vs. Ag/AgCl) (sweep rate: 50 mV/sec) at room temperature in a nitrogen stream, followed by carrying out constant-potential electrolysis for 1 hr at a constant potential of +1.8 V.

A silver wire 7 on the surface of which AgCl was deposited by electrolysis was wound around the Teflon tube 5 of the BPG electrode and served as a reference electrode and counter electrode in the oxygen sensor.

The BPG electrode and Ag/AgCl electrode were covered with a silicone tube 9 (having an inner diameter of 2 mm, a thickness of 0.5 mm and a sensing side thickness of 0.1 mm) filled with an aqueous solution 8 of 10% polyvinyl alcohol (containing a 50 mmol/l phosphate buffer solution at pH 7.38 and 0.154 mol/l NaCl) was used as the electrolyte. The periphery of the resulting structure was then fixed and insulated by a thermoplug 10 and a urethane cement 19. An oxygen sensor 20 was thus perfected.

(Experiment 4)

Figure 12:
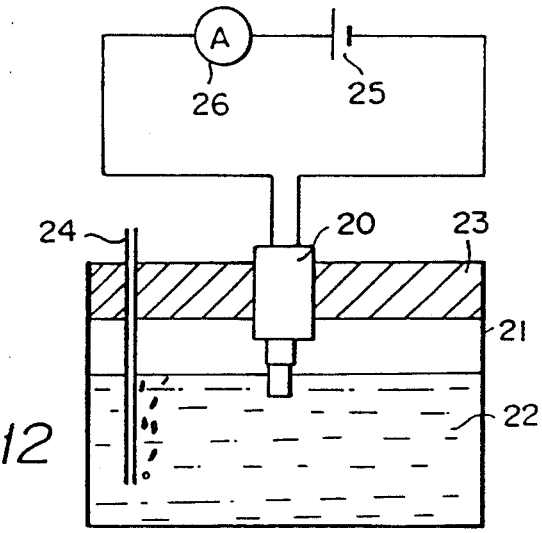
FIG. 12 is a circuit diagram showing an example of a measurement circuit using the oxygen sensor fabricated in accordance with the third embodiment.

FIG. 12 shows an example of a partial pressure measurement circuit using the oxygen sensor 20 fabricated in accordance with Example 3. The circuit includes an electrolytic cell 21, a liquid specimen 22, a plug 23, a gas injecting tube 24, a 0.6 V DC power supply 25 and a DC ammeter 26. The measurement circuit was used to measure the partial pressure of oxygen. A 50 mmol/l phosphate buffer solution containing 0.154 mol/l NaCl was used as the liquid specimen 22, the solution was saturated with a mixed gas of $N_2$ and $O_2$ of a known mixture ratio by means of the gas injection tube 24, thereby varying the partial pressure of oxygen, and the value of the current that flowed was measured by the EC ammeter 26. The results obtained are shown in Table 2, and a plot of the current density against the partial pressure of oxygen is illustrated in FIG. 13, from which it will be understood that an excellent linear relationship is established between the two. Measurements were taken at 25±0.1° C.

As a result, the partial pressure of oxygen dissolved in solution can be calculated from current (expressed in the form of current density). Table 3 shows the relationship between $PO_2$ (mmHg), calculated taking vapor pressure into consideration, and the mixed gas concentration (percent by volume) at various temperatures.

(Experiment 5)

It is understood that a linear relationship is established between the partial pressure of oxygen and current density in Experiment 4. Assuming that the reduction reaction of $O_2$ in the present oxygen sensor has its rate determined by the diffusion of $O_2$, the current value obtained will be expressed by the following equation upon performing a transformation, which takes the measurement conditions and the like into consideration, in accordance with the Cottrell equation:

$$|I| = A_o e^{-1/(R \cdot T)} \cdot PO_2 + I_o$$

where $A_o$, R are constants, T is the absolute temperature and $I_o$ is a residual current. Substituting "slope" for the slope of the straight line and taking the log of both sides gives us $$\log(slope) = A \cdot (1/T) + B \tag{1}$$

where $A = -1/R$, $B = \log A_o$

As the result of taking measurements in the same way as Experiment 4 and with the same measurement circuit while varying the temperature of the liquid specimen to 15° C., 25° C., 30° C., 37° C. and 40° C., it was found that PO$_2$ and current density exhibit good linearity, just as in Experiment 4, at each temperature, as illustrated in Table 4.

Figure 14:
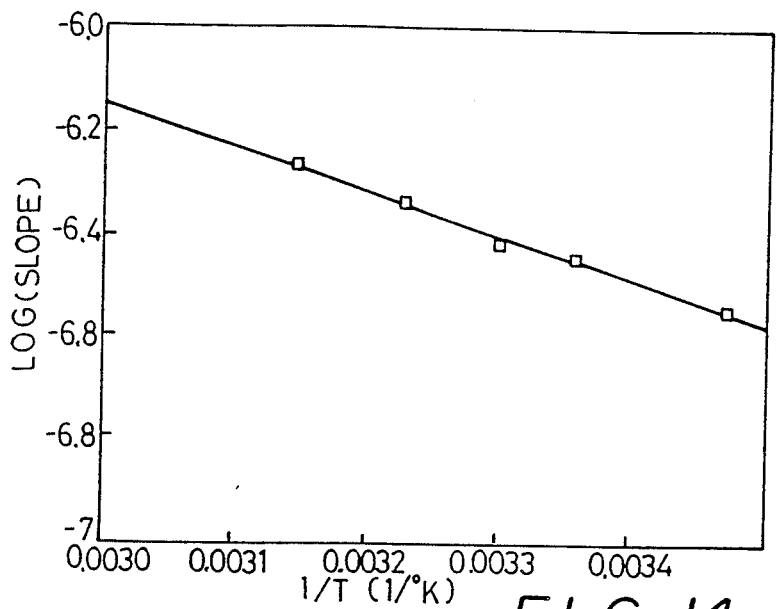
FIG. 14 is a graph in which the log of the slope of a $PO_2$-current line (a straight line) is plotted against the reciprocal of absolute temperature.

The slopes of the straight lines and the logarithms of these slopes are gathered together in Table 5, and a plot of the logarithm of slope against the reciprocal of absolute temperature is shown in FIG. 14. A good linear relationship holds between the logarithm of the slope and the reciprocal of absolute temperature, which is in agreement with theoretical formula (1).

Figure 15:
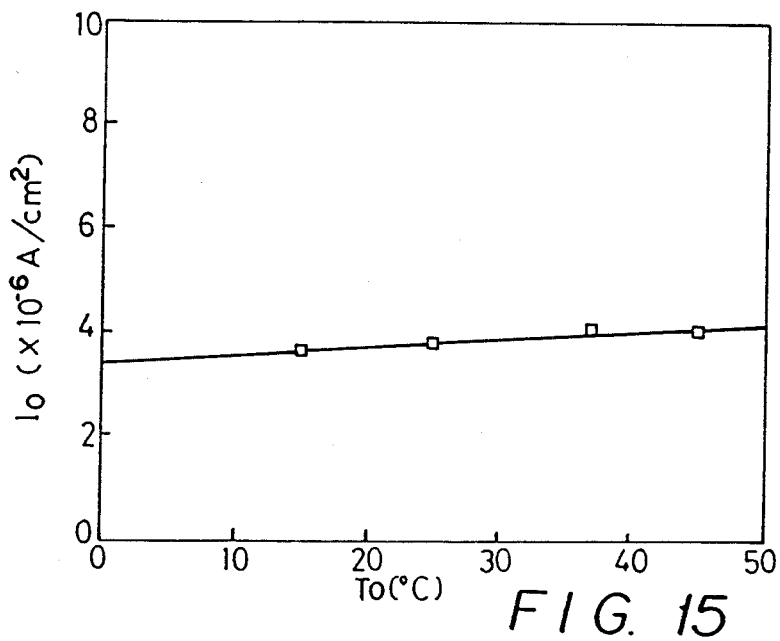
FIG. 15 is a graph in which an intercept of the $PO_2$-current line (a straight line) is plotted against temperature (° C.)

Table 6 shows values of residual current at each temperature, and FIG. 15 is a plot of residual current values against temperature (see FIG. 13 residual current values at 25±0.1° C.). As a result, it was clarified that residual current is expressed by the following equation as a function of temperature:

$$I_o = C \cdot T_o + D \tag{2}$$

Accordingly, the relationship between PO$_2$ and current density can be expressed by the following equation, which takes temperature compensation into account:

$$|I| = e^{(A/T+B)} \cdot PO_2 + C \cdot T_o + D \tag{3}$$

where T is absolute temperature and $T_o$ is the temperature in degrees Celsius.

By using the above relationships, oxygen sensor current values $i_1$, $i_2$, $i_3$, $i_4$ were measured at a total of four points, namely at two sets of temperatures and two sets of oxygen partial pressures, and these values were substituted into Eqs. (1), (2) to obtain the coefficients A, B, C, D, whereby it was found that the temperature calibration formula (3) could be evaluated.

(Experiment 6)

A temperature calibration was made using a four-point calibration method for obtaining the current density of the oxygen sensor at two known partial pressures of a concentration under various temperature conditions (a minimum of two different temperatures, e.g. 15° C. and 45° C.). Examples of the partial pressure: 37.36 mmHg and 134.5- mmHg at 15° C. This will now be described in sequence. Table 7 shows the four-point conditions used in calibration temperature, mixed gas concentration (volume %) and oxygen partial pressure PO$_2$ (mmHg) as well as the oxygen reduction current density (A/cm$^2$) of the oxygen sensor actually measured at the four points. Using these values, relations of current density vs. oxygen concentration at 15° C. and 45° C. are obtained in accordance with the equations:

$$15° \text{ C.:} \ I = \frac{i_2 - i_1}{PO_{2\text{-}2} - PO_{2\text{-}1}} \times PO_2 + I_o \tag{4-1}$$

$$45° \text{ C.:} \ I = \frac{i_4 - i_3}{PO_{2\text{-}4} - PO_{2\text{-}3}} \times PO_2 + I_o' \tag{4-2}$$

The expressions obtained are as follows:

$$15° \text{ C.:} \ |I|(A/cm^2) = 2.858 \times 10^{-7} \times \tag{5}$$

$$PO_2(mmHg) + 3.163 \times 10^{-6}$$

$$45° \text{ C.:} \ |I|(A/cm^2) = 5.406 \times 10^{-7} \times \tag{6}$$

$$PO_2(mmHg) + 4.148 \times 10^{-6}$$

Substituting the slopes of Eqs. (5), (6) and the intercepts in Eqs. (1), (2) of Experiment 5 and obtaining the coefficients A, B, C, D gives us

A = 2.125 × 10$^{-2}$
B = 2.188
C = 3.283 × 10$^{-8}$
D = 2.571 × 10$^{-6}$

The formula for calibrating the present oxygen sensor is expressed by the following:

$$|I| = \exp(2.125 \times 10^{-2}/T + 2.188) \cdot PO_2 + \tag{7}$$

$$3.282 \times 10^{-8} \times T_o + 2.671 \times 10^{-6}$$

A specific example of a temperature compensation at 30° C. using the calibration formula (7) will now be illustrated.

Evaluating the calibration formula of the oxygen sensor at 30° C. upon substituting T = 30 + 273 = 303(°K) gives $$|I|(A/cm^2) = 3.993 \times 10^{-7} \cdot PO_2(mmHg) + 3.656 \times 10^{-6} \tag{8}$$

Figure 16:
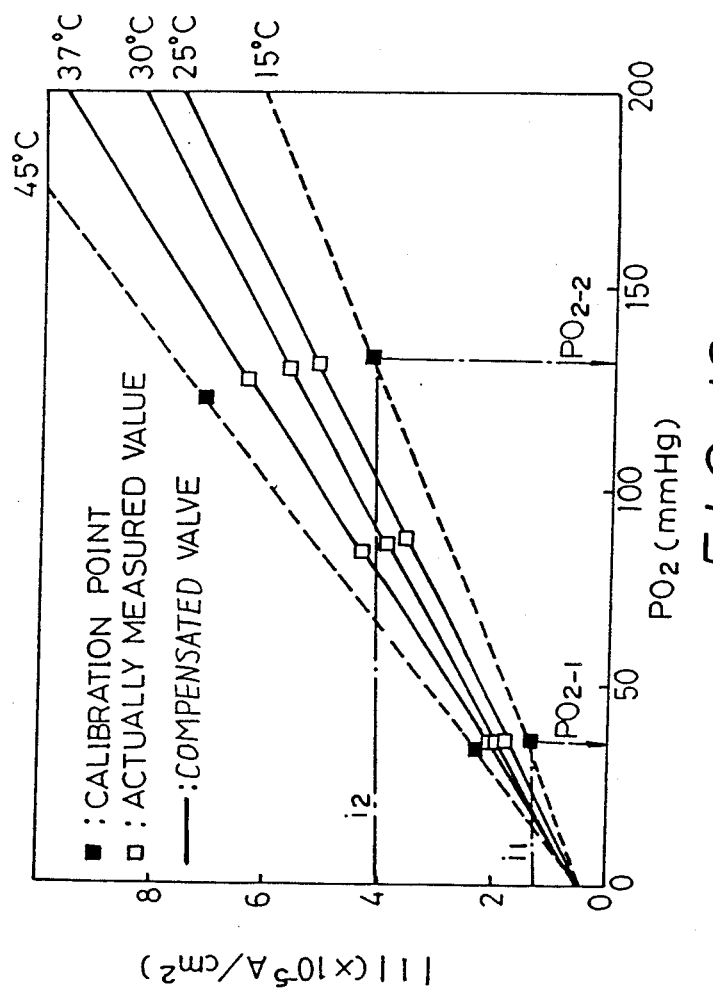
FIG. 16 is a graph showing a comparison between calibration straight lines and actually measured values.

(See the solid lines in FIG. 16.)

Using a method similar to that of Experiment 4, the reduction current density of the oxygen sensor was measured at 30° C., the actually measured values were collected together in Table 8, and these values were plotted, as indicated by the blank boxes in FIG. 16. As a result, it was found that the calibration formula (the solid lines in FIG. 16) and the actually measured values at 30° C. have a correlation coefficient of 0.999, thus exhibiting good agreement. It was clarified that a highly precise temperature compensation could be performed using the calibration formula (3).

(Experiments 7, 8)

As the result of measurements taken by a similar method at temperatures of 37° C. and 25° C., it was found that a highly precise temperature compensation could be performed just as at 30° C.

(Experiment 9)

Figure 17:
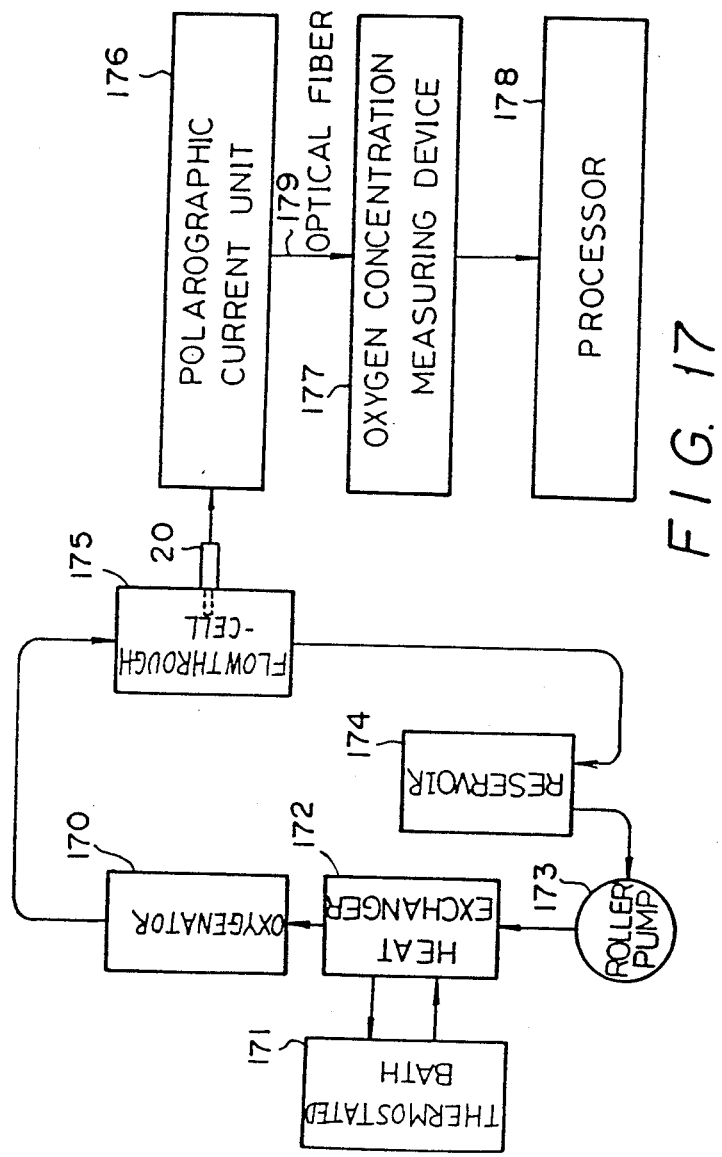
FIG. 17 is a block diagram showing an oxygen measurement set-up in the circulating system of an oxygenator apparatus.

Using an oxygen sensor temperature-compensated in accordance with Experiment 6, the PO$_2$ of a circulating system having an oxygenator apparatus was measured with a measurement solution (a 50 mmol/l phosphate buffer solution at pH 7.38 and a 0.154 mol NaCl adjusting solution) and the flow sheet shown in FIG. 17 includes an oxygenator 170, an thermostated bath 171 a heat exchanger 172, a roller pump 173, a reservoir 174, a flow-through cell 175 for setting the oxygen sensor 20, a polarographic ammeter 176, an oxygen concentration measuring device 177, and a processor 178. The polarographic ammeter 176 and oxygen concentration measuring device 177 are connected by an optical fiber 179.

Figure 18:
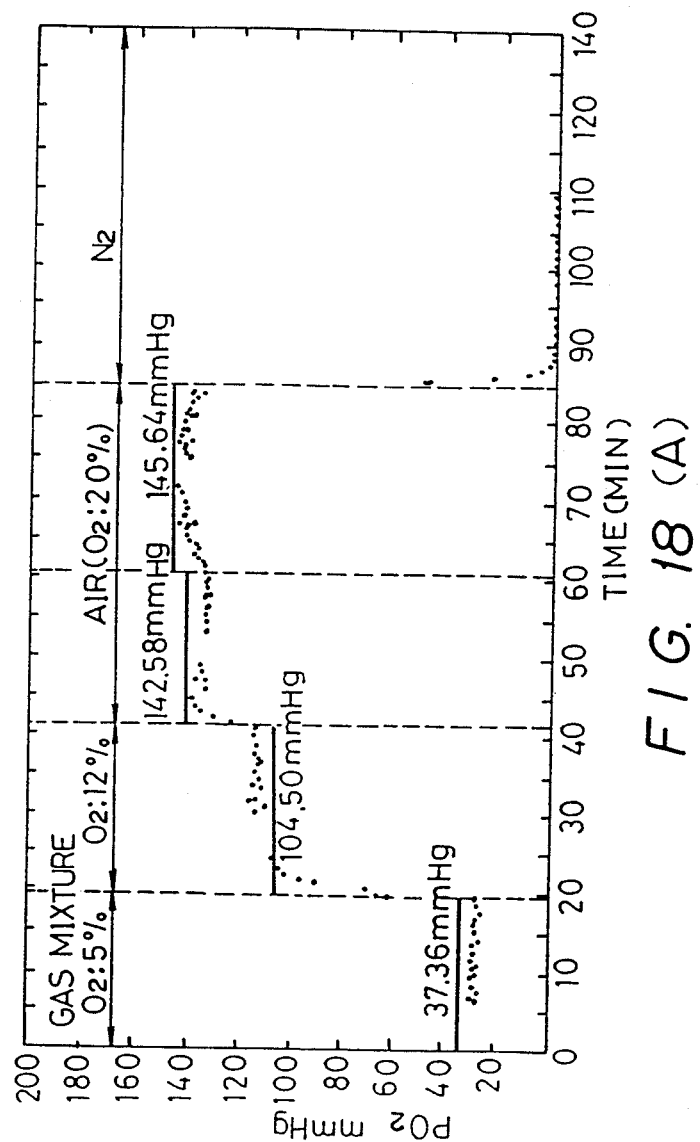
FIGS. 18(A)–(C) are views illustrating the results of measurements performed using the oxygen measurement system of FIG. 17.
Figure 18:
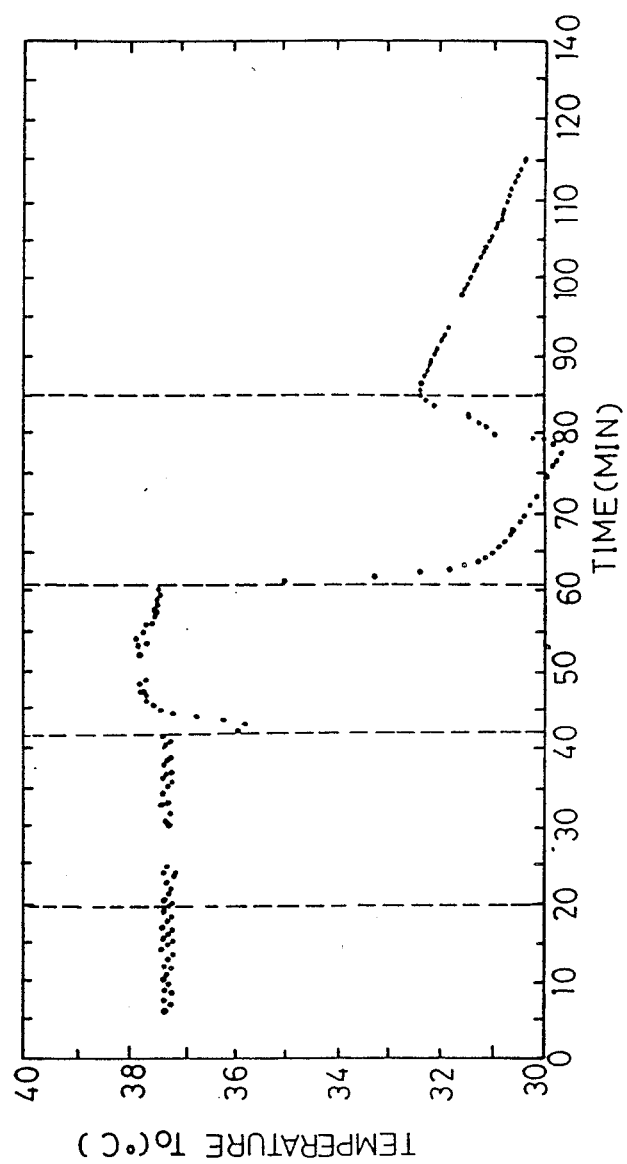
Figure 18:
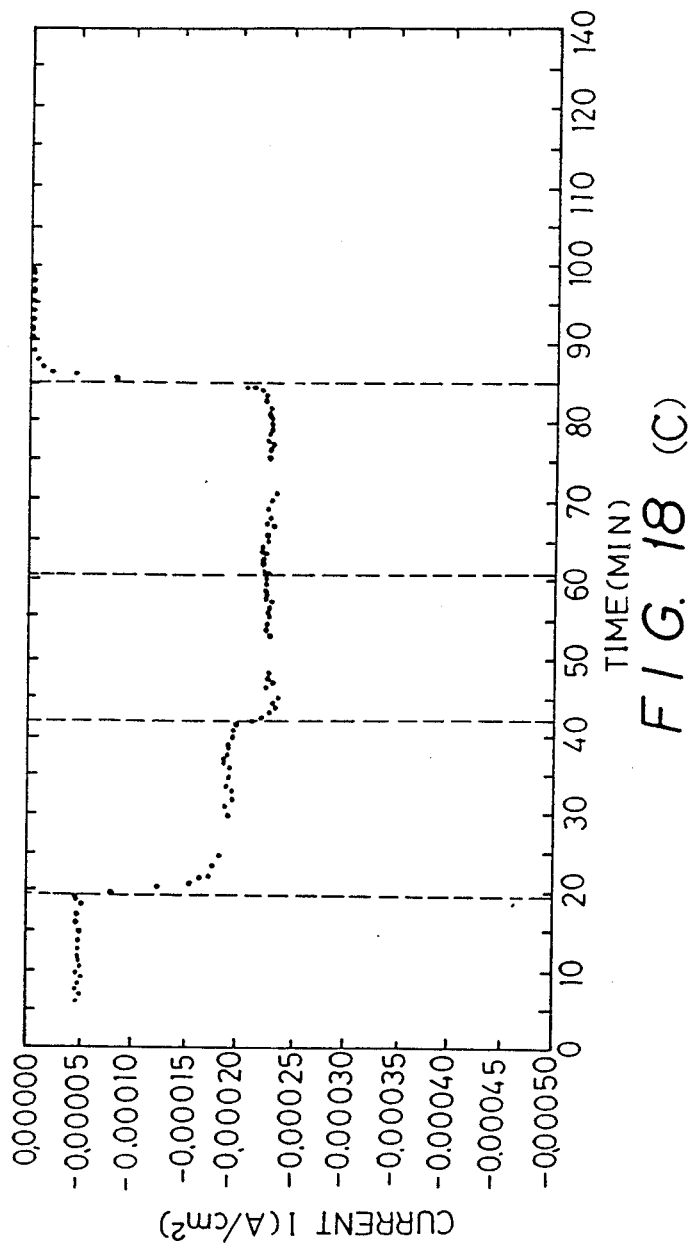

FIGS. 18(B), (C) and (A) illustrate the change in temperature within the system, the change in the reduction current of the oxygen sensor at such time, and the change in continuous measurement (whereby the mixed gas pressure was varied), calculated in terms of PO$_2$, respectively. It was clarified that the actually measured values (indicated by the dotted lines) are in good agreement with the change in PO$_2$. Thus it was verified that the present oxygen sensor can be used in a circulating system.

TABLE 1

| Response Time | PO$_2$ = →143 mmHg | PO$_2$ = 143→ mmHg | |
|---|---|---|---|
| 95% Response | 13.3 Sec. | 100.4 Sec. | From FIG. 9 |
| 99% Response | 27.1 Sec. | 146.6 Sec. | From FIG. 9 |

TABLE 2

| Mixed Gas Concentration (Vol. %) | 0 | 5 | 12 | 18 |
|---|---|---|---|---|
| PO$_2$ (mmHg) | 0 | 36.81 | 88.35 | 132.52 |
| Current Density (A/cm$^2$) | $3.81 \times 10^{-6}$ | $1.667 \times 10^{-5}$ | $5.628 \times 10^{-5}$ | $5.120 \times 10^{-5}$ |

TABLE 3

| Mixed Gas Concentration (Vol. %) | PO$_2$ (mmHg) | | | | |
|---|---|---|---|---|---|
| | 15° C. | 25° C. | 30° C. | 37° C. | 45° C. |
| 0 | 0 | 0 | 0 | 0 | 0 |
| 5 | 37.36 | 36.81 | 36.41 | 35.64 | 34.41 |
| 12 | 89.67 | 88.35 | 87.38 | 85.55 | 82.57 |
| 18 | 134.50 | 132.52 | 131.07 | 128.33 | 123.33 |
| Vapor Pressure | 12.784 | 23.755 | 31.825 | 47.076 | 71.899 |

TABLE 4

| 15° C. | PO$_2$ (mmHg) | 0 | 37.36 | 89.67 | 134.50 |
|---|---|---|---|---|---|
| | I (A/cm$^2$) | $3.622 \times 10^{-6}$ | $1.384 \times 10^{-5}$ | $3.038 \times 10^{-5}$ | $4.160 \times 10^{-5}$ |
| 25° C. | PO$_2$ (mmHg) | 0 | 36.81 | 88.35 | 132.52 |
| | I (A/cm$^2$) | $3.81 \times 10^{-6}$ | $1.677 \times 10^{-5}$ | $3.628 \times 10^{-5}$ | $5.120 \times 10^{-5}$ |
| 30° C. | PO$_2$ (mmHg) | 0 | 36.41 | 87.38 | 131.07 |
| | I (A/cm$^2$) | $4.03 \times 10^{-6}$ | $1.953 \times 10^{-5}$ | $3.915 \times 10^{-5}$ | $5.594 \times 10^{-5}$ |
| 37° C. | PO$_2$ (mmHg) | 0 | 35.64 | 85.55 | 128.33 |
| | I (A/cm$^2$) | $4.12 \times 10^{-6}$ | $2.063 \times 10^{-5}$ | $4.322 \times 10^{-5}$ | $6.327 \times 10^{-5}$ |
| 45° C. | PO$_2$ (mmHg) | 0 | 34.41 | 82.57 | 123.33 |
| | I (A/cm$^2$) | $4.084 \times 10^{-6}$ | $2.275 \times 10^{-5}$ | $4.486 \times 10^{-5}$ | $7.111 \times 10^{-5}$ |

TABLE 5

| Temperature (°C.) | 15 | 25 | 30 | 37 | 45 |
|---|---|---|---|---|---|
| Slope (A/cm$^2$ · mmHg) | $2.867 \times 10^{-7}$ | $3.603 \times 10^{-7}$ | $3.847 \times 10^{-7}$ | $4.599 \times 10^{-7}$ | $5.405 \times 10^{-7}$ |
| log (Slope) | −6.543 | −6.443 | −6.415 | −6.337 | −6.267 |

TABLE 6

| Temperature (°C.) | 15 | 25 | 30 | 37 | 45 |
|---|---|---|---|---|---|
| Intercept (Residual Current) (A/cm$^2$) | $3.62 \times 10^{-6}$ | $3.81 \times 10^{-6}$ | $4.03 \times 10^{-6}$ | $4.12 \times 10^{-6}$ | $4.08 \times 10^{-6}$ |

TABLE 7

| Temperature (°C.) | 15 | | 45 | |
|---|---|---|---|---|
| Mixed Gas Concentration (Vol. %) | 5 | 18 | 5 | 18 |
| PO$_2$ (mmHg) | 37.36 | 134.50 | 34.41 | 123.86 |
| Current Density (A/cm$^2$) | $1.384 \times 10^{-5}$ | $4.16 \times 10^{-5}$ | $2.275 \times 10^{-5}$ | $7.111 \times 10^{-5}$ |

TABLE 8

| Temp. °C. | Mixed Gas Concentration (Vol. %) | 0 | 5 | 12 | 18 |
|---|---|---|---|---|---|
| 25 | PO$_2$ (mmHg) | 0 | 36.81 | 88.35 | 132.52 |
| | Current Density (A/cm$^2$) | $3.81 \times 10^{-6}$ | $1.677 \times 10^{-5}$ | $3.628 \times 10^{-5}$ | $5.120 \times 10^{-5}$ |
| 30 | PO$_2$ (mmHg) | 0 | 36.41 | 87.38 | 131.07 |
| | Current Density (A/cm$^2$) | $4.03 \times 10^{-6}$ | $1.953 \times 10^{-5}$ | $3.915 \times 10^{-5}$ | $5.594 \times 10^{-5}$ |
| 37 | PO$_2$ (mmHg) | 0 | 35.64 | 85.55 | 128.33 |
| | Current Density (A/cm$^2$) | $4.12 \times 10^{-6}$ | $2.063 \times 10^{-5}$ | $4.322 \times 10^{-5}$ | $6.327 \times 10^{-5}$ |

What is claimed is:

1. An oxygen sensor comprising:
   an electrically conductive substrate whose potentiometric response is substantially unaffected by the presence of oxygen gas; and
   an electrolytic oxidative polymeric membrane adherently and substantially uniformly coating a surface of said electrically conductive substrate, said electrolytic oxidative polymeric membrane being formed by electrolytic polymerization and comprising at least one substance selected from porphyrin compounds and metal complexes thereof.

2. The oxygen sensor according to claim 1, wherein said electrically conductive substrate is selected from among electrically conductive carbon, indium tin oxide, iridium oxide, nickel or gold.

3. The oxygen sensor according to claim 1, wherein said porphyrin compound is selected from porphyrin compounds in which a hydroxy aromatic derivative is substituted at the meso-position and a porphyrin compound in which an amino aromatic derivative is substituted at the meso-position.

4. The oxygen sensor according to claim 1, wherein said metal complex of the porphyrin compound is selected from metallo-porphyrin complexes in which a hydroxy aromatic derivative is substituted at the meso-position and a porphyrin metal complex in which an amino aromatic derivative is substituted at the meso-position.

5. The oxygen sensor according to claim 1, wherein said complex-forming metal of porphyrin complex is a metal selected from the group consisting of Fe, Co and Ni.

6. The oxygen sensor according to claim 1, wherein said complex-forming metal of porphyrin complex is selected from the group consisting of titanium, vanadium, chromium, manganese, copper, ruthenium, rhodium, palladium, iridium, silver, gold, zinc and tin.

7. An oxygen sensor comprising:

an electrically conductive substrate whose potentiometric response is substantially unaffected by the presence of oxygen gas; and an electrolytic oxidative polymeric membrane coating a surface of said electrically conductive substrate, said electrolytic oxidative polymeric membrane comprising at least one substance selected from porphyrin compounds in which a hydroxy aromatic moiety is substituted at the meso-position, porphyrin compounds in which an amino aromatic moiety is substituted at the meso-position, and metal complexes thereof.

8. An oxygen sensor comprising:

an electrically conductive substrate whose potentiometric response is substantially unaffected by the presence of oxygen gas; and an electrolytic oxidative polymeric membrane coating a surface of said electrically conductive substrate, said electrolytic oxidative polymeric membrane comprising at least one substance selected from porphyrin compounds and metal complexes thereof, wherein the complex-forming metal is a transition metal selected from the group consisting of titanium, vanadium, chromium, manganese, copper, ruthenium, rhodium, palladium, iridium, platinum, silver and gold.

* * * * *